US007544513B2

(12) United States Patent
Blomberg et al.

(10) Patent No.: US 7,544,513 B2
(45) Date of Patent: Jun. 9, 2009

(54) HEMOGLOBIN ASSAY FOR NEONATAL SCREENING

(75) Inventors: Kaj Blomberg, Turku (FI); Pasi Kankaanpaa, Parainen (FI); Thomas Campbell, North Canton, OH (US)

(73) Assignee: Wallac Oy, Turku (FI)

( * ) Notice: Subject to any disclaimer, the term of this patent is extended or adjusted under 35 U.S.C. 154(b) by 433 days.

(21) Appl. No.: 10/946,311

(22) Filed: Sep. 22, 2004

(65) Prior Publication Data
US 2005/0118654 A1    Jun. 2, 2005

Related U.S. Application Data

(60) Provisional application No. 60/504,962, filed on Sep. 23, 2003.

(51) Int. Cl.
    G01N 33/72    (2006.01)
(52) U.S. Cl. .......................... 436/66; 435/7.1; 435/7.25; 435/7.92; 435/7.94; 435/973; 436/519; 436/522; 436/524; 436/528; 436/548; 436/15; 436/164; 436/172; 436/811
(58) Field of Classification Search ................ 435/7.1, 435/7.2, 7.9, 7.92, 7.94, 287.2, 968, 973, 435/7.25; 436/517, 519, 522, 525, 548, 15–18, 436/164, 177, 178, 811, 524, 528, 66, 172; 422/55, 61
See application file for complete search history.

(56) References Cited

U.S. PATENT DOCUMENTS 6,617,158 B1    9/2003    Bohmer 6,951,760 B2 * 10/2005 Hofstraat .................... 436/172

FOREIGN PATENT DOCUMENTS

EP    1 255 111 A1    11/2002

OTHER PUBLICATIONS

Rosenthal et al., Monoclonal antibody immunoassay for the identification of hemoglobin variants in neonatal screening, Screening 3: 67-76 (1994).*
Moscoso et al., Peroxidase/Monoclonal antibody Conjugates for the Study of Hemoglopathies, Journal of Laboratory Analysis 7: 214-219 (1993)).*
Turpeinen et al., Determination of Fetal Hemoglobin by Time-Resolved Immunofluorometric Assay (Clin. Chem. 38(10): 2013-2018 (1992).*
Campbell et al., Detection of Hemoglobin Variants in Erythrocytes by Flow Cytometry, Cytometry 35: 242-248 (1999).*
Moscoso et al., "Peroxidase/Monoclonal Antibody Conjugates for the Study of Hemoglobinopathies," *Journal of Clinical Laboratory Analysis*, 1993, vol. 7, pp. 214-219, Wiley-Liss, Inc., New York, New York, U.S.A.
Rosenthal et al., "Monoclonal antibody immunoassay for the identification of hemoglobin variants in neonatal screening," *Screening*, 1994, vol. 3, pp. 67-76, Elsevier Science Publishers B.V., London, England.

* cited by examiner

Primary Examiner—Gailene R Gabel
(74) Attorney, Agent, or Firm—Buchanan Ingersoll & Rooney PC

(57) ABSTRACT

The present invention provides an assay, suitable for neonatal screening of hemoglobinopathies by quantitatively determining the presence of at least one pair of hemoglobin (Hb) variants, determining the ratio between the signals obtained from each variant; and, based on that ratio, determining whether the tested subject is afflicted or not.

9 Claims, 2 Drawing Sheets

HEMOGLOBIN ASSAY FOR NEONATAL SCREENING

FIELD OF THE INVENTION

The present invention relates to methods for neonatal screening of hemoglobinopathies. More specifically the present invention relates to immunoassays for neonatal screening of hemoglobinopathies. Also disclosed are reagent combinations and kits for use in such assays.

BACKGROUND OF THE INVENTION

Human hemoglobins are tetramers of globin chains folded around four heme groups. The tetramer has a molecular weight of approximately 64,500. A functional hemoglobin (Hb) is composed of two alpha ($\alpha$) globin chains and two non-alpha ($\beta$, $\gamma$ or $\delta$) chains. A total of eight functional globin chains are found in various stages of development, producing eight types of normal Hb tetramers. Adults have predominantly HbA ("normal" or "common" hemoglobin) and a small amount of $HbA_2$. The hemoglobin of newborns is comprised mainly of fetal hemoglobin (HbF), of about ~15-40% is HbA. Fetal hemoglobin comprises only a barely detectable level of $HbA_2$.

As a result of mutations in the genes encoding the different Hb-chains, there are more than 700 known variant hemoglobins. The majority of these variants are due to substitutions of amino acids on a single globin chain. Most of the mutations produce no clinically significant abnormal Hb function. Less than ten of the variants cause severe disease conditions, so called hemoglobinopathies.

The variant hemoglobins are geographically unevenly distributed and occur at different frequency in different areas. The earliest identified and clinically most significant variant is HbS, which relates to sickle cell anemia. The HbS variant hemoglobin is traditionally most abundant in populations of African and Mediterranean ethnicity. Due to increased ethnic diversity in most countries hemoglobinopathies seem to become more common also in Europe and the U.S.A. The birth prevalence of sickle cell anemia has increased by almost 50% over one decade in U.K. and the overall estimated prevalence for U.K. (1:2380) is even higher than many other inherited diseases, such as cystic fibrosis or phenylketonuria. Sickle cell anemia is a very severe disease, approximately 20% of children with the disease die within the first two years, often by infections. An early neonatal identification of this hemoglobinopathy substantially decreases the mortality and morbidity during the first five years of life. Heterozygotes (HbAS) show no symptoms.

Other important Hb variants include HbE, which is the second most frequent hemoglobinopathy, and occurs predominantly in Asia. HbC occurs most frequently in western parts of Africa. Other common hemoglobin variants are HbG and HbD.

Some of the variant hemoglobins, such as HbS, occur at such a high frequency that routine screening of newborns to identify possibly afflicted subjects is recommended. In some areas, such as most states of the United States and in Brazil, all newborn babies are subjected to neonatal testing for possible sickle trait, and other countries are considering adding universal neonatal screening programs to their national health care programs. Universal neonatal hemoglobinopathy screening programs are recommended in e.g., United Kingdom in areas where the minority ethnic population of African origin exceeds 15%. Central Middlesex Hospital in north-western London tests all babies born in the North Thames (West) healt region, i.e., ~50 000 births per year (Campbell et al. in Clin Chem, 45:7, 969-975, 1999).

Other hemoglobin variants considered to be included in routine neonatal screening are e.g., HbC, HbD-Punjab, and Hb-Barts. All of these hemoglobin variants are characterized by mutations leading to amino acid substitutions in the $\beta$-chain. Abnormal hemoglobins due to mutations in the $\alpha$-chain are relatively uncommon.

Thalassemias are diseases caused by mutations in the hemoglobin $\alpha$-chain, leading to diminished production of hemoglobin. A distinction is made between $\alpha$- and $\beta$-thalassemia. Normally the $\alpha$-globin chain is present as a double copy. Individuals with $\alpha$-thalassemia has reduced or no synthesis of the alpha-chain. Alpha-thalassemia is usually detected in newborns by the presence of Hb-Bart's $\gamma$-chains. Beta-thalassemia is characterized by a reduction or absence of $\beta$-globin synthesis. Newborns with no $\beta$-globin chains will have no HbA and suffer from severe anemia. $\beta^0$-thassemia or $\beta$-thalassemia major usually results in death during childhood. Individuals with reduced synthesis of $\beta$-globin chains will show reduced HbA, and in some case slightly elevated $HbA_2$. As the prevalence of thalassemias is high, there is also a need to include thalassemia detection in routine neonatal screening.

There is thus an established need for inexpensive and easy-to-use screening assays, which can distinguish a healthy subject from a possibly afflicted subject needing further testing to diagnose a possible hemoglobinopathy.

There are, however, no clinically applicable methods that would give a simple afflicted/non-afflicted answer. Presently available methods for detecting hemoglobinopathies are all based on techniques that separate and identify all different variant hemoglobins present in the sample. Such methods, based on electrophoresis, isoelectric focusing (IEF) or HPLC are very labor-intensive and expensive and therefore not suitable for universal routine neonatal screening of hemoglobinopathies.

Electrophoretic methods, such as IEF are based on the fact that the variant Hbs have different electric charge. One commercially available product based on IEF is the Wallac RESOLVE® Neonatal Hemoglogin test kit, which is designed to separate cord blood hemoglogin on a thin layer gel to allow differentiation between sickle cell anemia and sickle cell trait. The separation of HbF from HbA permits differentiation of sickle cell anemia (HbSS) from sickle cell trait (HbAS). The preparation and separation of hemoglobin is accomplished through the application of a hemoglobin sample onto a precast agarose gel containing RESOLVE® Ampholytes, pH 6-8. RESOLVE® Ampholytes are composed of low molecular weight amphoteric molecules with varying isoelectric points. When an electrical current is applied to the gel, these molecules migrate through the gel to their isoelectric points (pI) along the gel, forming a stable pH gradient.

The hemoglobin variants also migrate through the gel until they reach the area where their individual pI:s equal the corresponding pH of the gel. At this point, the net charges on the variants are zero and migration ceases. The electric field counteracts diffusion and the hemoglobin variant forms a discrete thin band. Hemoglobin bands may be visualized using Perkin-Elmer's JB-2 STAINING SYSTEM®.

IEF is today probably the method of choice in most clinical laboratories for detecting hemoglobinopathies. However, this method requires the physical handling of numerous gels and is prone to pipetting errors. Moreover, the interpretation of the result is based on physical examination of the gels, and requires highly skilled technicians and experts interpreting the results. Furthermore, the testing laboratories are required to store the gels for a specified time period, requiring storage capacity and suitable facilities for safe storage.

A significant drawback to gel electrophoresis methods is their inability to identify Bart's hemoglobin. Thus α-thalassemias may be missed in this approach.

Another available method of diagnosing hemoglobinopathies is based on high performance liquid chromatography, HPLC, described e.g., in U.S. Pat. No. 4,108,603 and U.S. Pat. No. 5,719,053. These methods are not as labor-intensive as IEF but a considerable amount of work-load is still needed. The capacity of HPLC might also be limiting, if applied to routine neonatal screening programs, as simultaneous analysis of multiple samples is not possible.

A survey of available laboratory methods and international guidelines concerning the screening of hemoglobinopathies may be found in e.g., Clinical Chemistry, 46:8(B), 1284-1290, 2000 and in Guideline: The Laboratory Diagnosis of Haemoglobinopathies, British J Haematol, 101, 783-792, 1998.

Absolute cost implications of the currently used hemoglobinopathy testing programs are difficult to estimate. Davies et al. in Health Technology Assessment 2000 estimate that the cost per baby when testing 50,000 newborns using IEF was £3.51 and £3.83 when using HPLC, that is £1.7 million for 500,000 births. At a prevalence of 1:2000 the costs thus rise to about £6700 per detected case. The overall cost per case detected has been approximated to £20,000 for the whole of United Kingdom.

Moscoso et al. describes in J Clin Lab Anal., 7(4), 214-19, 1993, an ELISA assay for differential diagnosis of hemoglobinopathies. They describe the use of monoclonal antibodies for normal and variant hemoglobins. Such a test is useful for diagnostic purposes and for specific identification of hemoglobin variants, but the need of including reagents for all known variants in the test, does not make it suitable for neonatal screening purposes.

Rosenthal et al, describes in Screening, 3(2), 67-76, 1994, monoclonal antibody assay HEMOCARD-kits for the identification of HbA, HbS, HbC and HbE. The test is useful for confirming the presence of variant hemoglobins, but again, it is not useful for neonatal screening purposes.

One common property of the above described methods for detecting hemoglobinopathies is the fact that they actually provide too much information to be useful as screening tests—in fact the current methods are useful as confirmatory diagnostic tests. An ideal screening program should identify only those at risk for a given disease, e.g. sickle cell disease (SCD). For example, in some health care systems sickle cell disease is the only hemoglobinopathy allowed to be reported. Thus, a screening test should primarily find the diseased group of interest. There is thus an established need of easy-to-use, inexpensive assays suitable for neonatal screening of hemoglobinopathies.

BRIEF DESCRIPTION OF THE INVENTION

The present invention discloses a method for neonatal screening of hemoglobinopathies. The method is performed on a blood sample derived from a newborn and utilizes at least one pair of differently labelled variant hemoglobin specific reagents specifically recognizing different hemoglobin variants. Optionally an additional third reagent used in the method recognises a determinant common to hemoglobin. The reagents are allowed to bind to any hemoglobin present in the sample and the formed hemoglobin-reagent complexes are detected by means of said labels. Then the ratio between the signals achieved from the labelled reagents is calculated, and based on this ratio, it is possible to determine whether the sample is derived from a non-afflicted sub-ject or from a possibly afflicted subject in need of further testing and diagnosing of a possible hemoglobinopathy.

In a preferred embodiment, the differently labelled reagent pair is detected in one undivided sample, but if desired the sample may be divided into two separate reaction chambers, said first member of the reagent pair and said third reagent being added to a first reagent chamber and said second member of the reagent pair and said third reagent being added to a second reagent chamber.

In a preferred embodiment of the present invention said first member of the variant hemoglobin specific reagent pair is a monoclonal antibody, recognizing e.g., HbA, said second member of the variant hemoglobin specific reagent pair is a monoclonal antibody recognizing e.g., HbS and said third reagent is a monoclonal antibody recognizing the hemoglobin α-chain.

Further disclosed are reagent combinations for use in a method according to the present invention, comprising at least one pair of labelled hemoglobin specific, differently labelled reagents, which specifically recognize different hemoglobin variants; and a third reagent recognizing a constant part of the neonatal hemoglobin, said third reagent comprising a capturing moiety or, optionally being coupled to a solid support.

Further disclosed are kits for use in neonatal screening for hemoglobinopathies, comprising at least one pair of labelled hemoglobin specific, differently labelled reagents, which specifically recognize different hemoglobin variants; a third reagent recognizing a constant part of the neonatal hemoglobin, said third reagent comprising a capturing moiety or, optionally being coupled to a solid support; and, optionally, buffers, wash solutions, signal generation and signal amplification reagents.

DETAILED DESCRIPTION OF THE INVENTION

Figure 1:
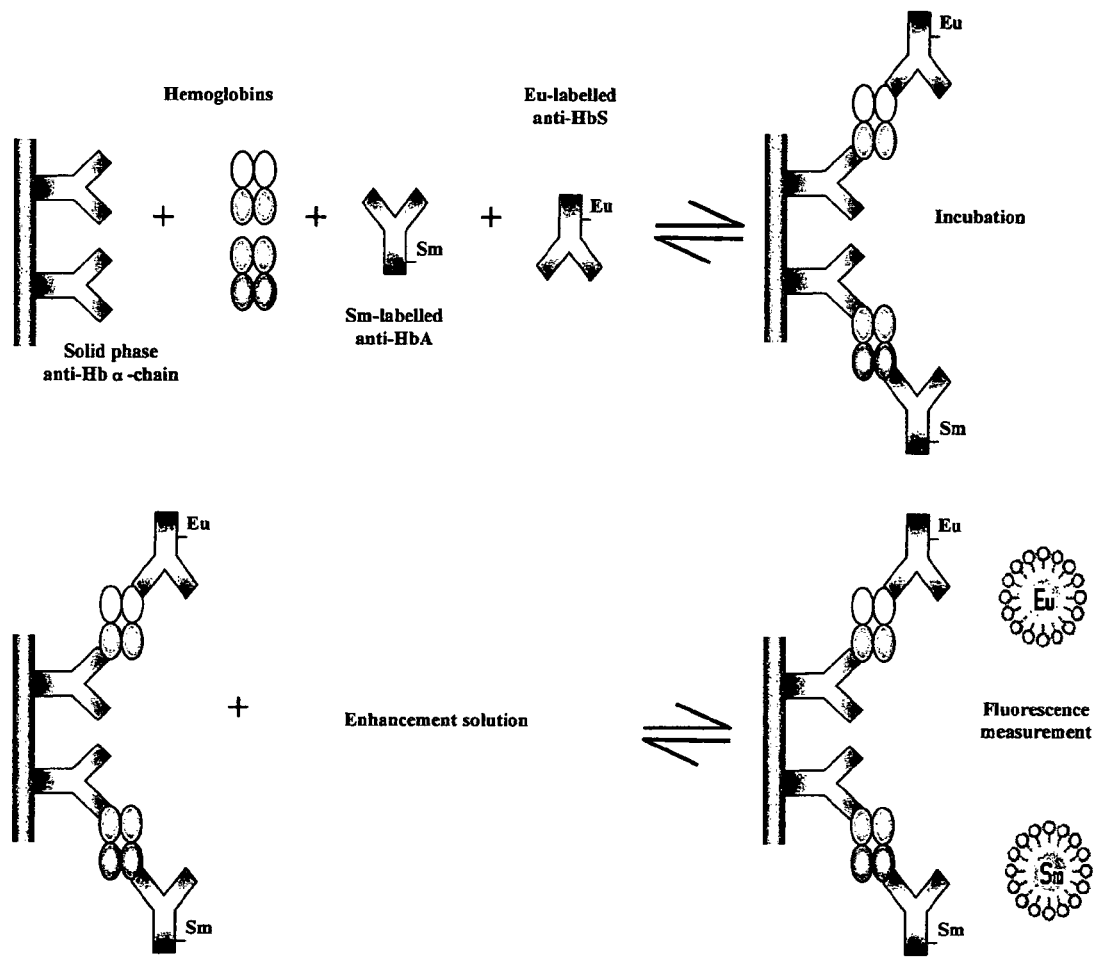
FIG. 1 is a schematic presentation of an immunoassay format for performing the method of the present invention.

The present invention is based on the perception that by simultaneously and quantitatively detecting the presence of at least one pair of variant Hb's in a blood sample, and determining the ratio between the signal obtained from each variant, it is possible to distinguish non-afflicted subjects from afflicted subjects or possibly afflicted subjects, such as carriers.

By choosing the pair of variant hemoglobins to be detected, the screening assay according to the present invention may be tailored so that geographical differences are accounted.

In one embodiment of the present invention a first member of the pair is a common Hb, such as HbA or HbF, preferably HbA, and the second member of the pair is a variant Hb chosen from the group consisting of e.g. HbS, HbC, HbD, HbE and HbF, wherein the choice of said second variant Hb is made based on the geographical region where the screening assay is to be performed.

It is thus an object of the present invention to provide an assay, suitable for neonatal screening of hemoglobinopathies by measuring the presence (or total Hb percentages) of at least one pair of hemoglobin variants, calculating the ratio of the two variants and, based on that ratio, determining whether the tested subject is afflicted or not. In another embodiment of the present invention the assay may be designed as to include more than one pair of variant hemoglobins to be analyzed, wherein the comparison of the signal ratio is performed for each pair, respectively.

In this method the presence of said hemoglobin variants is determined by any applicable quantitative method, such as an immunoassay, detection of aptamers or molecular imprints, tandem-MS-methods or microarrays. Other assay formats equally suitable in the present invention are homogeneous assay formats, such as FRET (Clinical Chemistry 45:6, 855-861, 2000). The achieved measurement is used to calculate the ratio between the variants. Based on this ratio, it is possible to distinguish carriers from afflicted and non-afflicted subjects. The method also gives a preliminary suggestion on what further specific tests need to be carried out, in case of carriers/afflicted subjects.

Monoclonal antibodies recognizing variant hemoglobin available, such as antibodies recognizing Hb α-chain (both common and zeta variant), HbA, HbS, HbE, HbC and HbF are known in the art. Such antibodies are available from e.g., PerkinElmer Life Sciences, as well as from common culture collections such as American Type Culture Collection.

According to one preferred embodiment of the present invention, there is provided an automated immunoassay detecting at least one pair of variant hemoglobins simultaneously from one undivided sample. The immunoassay is preferably a sandwich-type assay, wherein the hemoglobin present in the sample is captured onto a microtitration well or other equivalent solid support (e.g. beads, nanoparticles, glass and plastic surfaces, polymers) by the aid of an antibody against a particular globin chain, such as the alpha chain. At least one pair of differently labelled monoclonal antibodies, each member of said pair detecting different hemoglobin variants, e.g., HbA or HbF, and HbS, HbC or HbE, is added and antigen-antibody complex allowed to be formed. The signal obtained from the different labels of the antigen-antibody complex is quantitatively registered, e.g., by a DELFIA® type instrumentation, and the ratio of the signals is calculated. With this preferred automated system, the ratio is automatically calculated using accompanying data-management system (MULTICALC™) based on total Hb % results of each assessed Hb variant.

When calculating the ratios they are preferably compared to calibrated standard curves derived from pure variant tests. Possible differences in signal intensity due to the use of different labels may also be automatically corrected. Alternatively, cut-off determinations may be based on controls with known ratios of appropriate Hb variants.

Other assay formats known in the art are equally applicable, such as assay formats where the variant specific antibodies are captured on a solid support and the detection is performed by labels on the α-chain antibody. The coupling or capture onto a solid support may also be achieved by other types of binding, such as capture by an affinity pair such as biotin-streptavidin.

By determining suitable cut-off values for the evaluation of the results, the samples may be classified into three distinct groups, non-afflicted, non-afflicted carriers and afflicted. Based on this classification, it is possible to decide which samples need to be subjected to additional testing and specific diagnosis of the type of hemoglobinopathy.

In a preferred embodiment of the present invention the antibody pair is anti-HbA/HbS. Based on the automatically calculated ratio the blood sample may be interpreted by utilizing two different cut-off ratios:

| | |
|---|---|
| HbA/HbS RATIO > cut-off level A | non-afflicted |
| cut-off level A > HbA/HbS RATIO > cut-off level B | sickle trait (carrier) |
| HbA/HbS RATIO < cut-off level B | afflicted, needs confirmation of specific variant by additional testing. |

It is, of course, also possible to use only one cut-off value, chosen so that it does not distinguish between carriers and afflicted subjects, if it is desired only to screen out the non-afflicted. On the hand, it may be possible to choose additional cut-off values in order to distinguish between normal neonatal sample (FA) and sample containing other (than HbS) variants, e.g. the A to S ratio of FAD or FAC may differ from that of FA sample.

In addition to the above given example, the method of the present invention gives further, indicative information concerning α- and β-thalassemias. Lack of or diminished HbA and/or HbS signal, on the other hand, indicate a potential α- and/or β-thalassemia. The presence of some other common variant, such as HbC or HbD but no HbS in the sample, would still give a high HbA/HbS ratio (above cut-off level A), as no HbS signal is obtained. However, if one of these non-S variants is associated with HbS (e.g. SC disease), this will be detected as a ratio well below cut-off level B. In all these cases, affected subjects are identified and subjected to further diagnosis.

Even though indirect information concerning the other hemoglobinopathies, e.g. HbC related sickle cell disease, is obtained with the preferred method described above, the dual assay may be constructed more geographically focused if desired. For example, in Asia, the hemoglobin pair of choice could be HbA/HbE. Other preferred antibody-pairs suitable for use in hemoglobinopathy assays according to the present invention may thus include, e.g. HbA/HbF, HbA/HbC and HbA/HbD.

Labelling technologies that may be used for the simultaneous detection of two antibodies from an undivided sample may be based on, e.g., fluorescence, radioactivity, luminescence, chemiluminescence, time-resolved fluorometry, absorbance, fluorescence polarisation or fluorescence resonance energy transfer. Labelling may also be based on enzymatic reactions, colloidal sols or nanoparticles. A preferred method according to the present invention utilizes chelates such as Europium (Eu), Samarium (Sm), terbium (Tb) and dysprosium (Dy). Such fluorescent chelates are easily detected by automated DELFIA®-instrumentation, which is widely used in clinical laboratories all over the world. For use in homogeneous assay formats preferred labels include suitable luminescent donor/acceptor pairs, such as Europium/cyanine dyes (e.g. Cy3, Cy5, Cy7), Europium/phycobiliproteins (e.g. APC, C—PC, R—PC), Fluorescein/tetramethylrhodamine.

The DELFIA®-immunoassay format is a highly preferred format, but any assay format enabling a quantitative measurement of different hemoglobin variants from one undivided sample is equally useful in the present invention. Examples of such assay formats include homogeneous FRET-assays, tandem-MS-methods or the use of microarray techniques.

One advantage of the present invention is the fact that by detecting only two variants, e.g. HbA and HbS, a positive identification of a non-afflicted sample combined with an indicative result concerning possible disease-related variants requiring further testing is possible. If the sample contains other variants than the two measured, the ratio between the measured variants will give a result that is indicative of other possible disease-related variants as well, if desired. Thus, a screening assay according to the present invention is very useful in routine neonatal screening, where a definitive diagnosis is not needed or even desired, only a screen to determine which tested subjects need further testing and diagnosing.

The hemoglobinopathy screening assay according to the present invention may naturally be further elaborated to include the testing of further variants, for example by including additional variant antibodies or antibody pairs as described above. In such embodiments, the indicative value of the screening test is ameliorated, if desired. However, according to the guidelines of many health care programs a simple +/− result given by the two-variant screening assay is preferred.

Blood samples used in the methods and assays according to the present invention include dried blood spot specimens (DBSS), so-called Guthrie spots. This is an advantage of the present invention. Such samples are easily collected during check ups of the neonatals, and the possible contamination of umbilical cord blood by maternal blood is avoided. The sample handling is very simple in methods and assays according to the present invention. Where the assay format is an immunoassay performed on one undivided sample in a microtiter well, there is no need for supplementary sample pretreatment or extraction of blood from the filter paper. A small piece of the filter paper used for collecting the blood sample is punched out and placed in the microtiter well, where it does not interfere with the antibody-hemoglobin complex formation.

In addition to the sample handling being very simple, there are further advantages of the method according to the present invention. The stability of the blood sample poses no problem, and Guthrie spots are easily stored. Furthermore any errors due to pipeting errors are circumvented. The results of the assays according to the present invention are furthermore not affected by differences in the sample quality, as e.g., differences in total hemoglobin contents of the samples do not affect the measured ratios.

One further advantage related to the highly preferred assay format, the immunoassay, is the ease of automation of such methods as well as the ease of use, which removes the labor-intensity drawbacks of presently used assays.

It is a further object of the present invention to provide reagents and reagent combinations for use in neonatal screening of hemoglobinopathies. Such reagents and reagent combinations may comprise at least two reagents for detecting at least two hemoglobin variants. Preferred reagents are for example monoclonal antibodies specifically identifying one specific Hb-variant. However, many other types of reagents may be used in the method and assays according to the present invention, such as HB-variant specific aptamers or molecular imprints and so on (Analytical Chemistry 69, 345A-349A, 1997 and Journal of Biotechnology, 74(1), 5-13, 2000). Preferred reagent combinations include monoclonal antibody pairs detecting HbA/HbS, HbA/HbF, HbA/HbC and HbA/HbD. One especially preferred reagent combination comprises an HbA-specific monoclonal antibody and an HbS-specific monoclonal antibody.

Kits for use in the method and assay according to the present invention include reagents and reagent combinations, comprising at least two Hb-variant specific labelled anti-Hb antibodies (reagent pair), and at least one additional Hb-specific reagent, such as an Hb α-chain specific antibody, preferably coupled to a solid support. The kit may further include necessary buffers for reagent incubation, wash solutions for separating unbound reagents from the bound complexes, signal generation and/or amplification reagents, such as dissociative fluorescence enhancement solutions, enzyme substrates or chemiluminesence generating compounds. The choice of the optional reagents included in the kit according to the present invention, varies depending on the type of hemoglobin specific reagents, the assay format and on the labelling technology of choice.

Preferred kits according to the present invention may additionally include written instructions on how to determine the cut-off lines for distinguishing between samples derived from non-afflicted and possibly afflicted subjects, based on the measured and calculated signal ratios, e.g., by the use of an included algorithm. Such instructions may also be included as a separate computer program performing the categorization of the results.

The neonatal hemoglobinopathy screening assay will hereinafter be more specifically described by specific examples. The examples are, however, not to be interpreted as restricting the scope of the present invention. Other preferred embodiments are easily envisioned, as described above.

EXAMPLE 1

Labelling of Anti-HbA Antibody

Sm-N1 chelate was obtained from Wallac Oy, Turku, Finland. An anti-HbA antibody (PerkinElmer Life and Analytical Sciences, Akron, USA) at the concentration of 7.0 mg/mL was incubated with a 100-fold molar excess of the chelate in 50 mmol/L carbonate buffer, pH 9.5, overnight at +4° C. Labelled antibody was then separated from unreacted chelates by gel filtration (Protein G Sepharose) with the buffer containing 50 mmol/L Tric-HCl, pH 7.75, containing 9 g/L NaCl as elution buffer. The labelling degree ($Sm^{3+}$/IgG) was determined by measurement of the $Sm^{3+}$ concentration of conjugated antibody against a $Sm^{3+}$ calibrator with a DELFIA system. The labelling degree of 9.7 was achieved. Labelled antibody has been found stable for several months when stored at +4° C. in Tris buffer, pH 7.4, containing bovine serum albumin as a stabilator (0.1%).

EXAMPLE 2

Labelling of Anti-HbS Antibody

Eu-N1 chelate was obtained from Wallac Oy, Turku, Finland. An anti-HbS antibody (PerkinElmer Life and Analytical Sciences, Akron, USA) at the concentration of 2.4 mg/mL was incubated with a 100-fold molar excess of the chelate in 50 mmol/L carbonate buffer, pH 9.5, overnight at +4° C. Labelled antibody was then separated from unreacted chelates by gel filtration (Protein G Sepharose) with the buffer containing 50 mmol/L Tric-HCl, pH 7.75, containing 9 g/L NaCl as elution buffer. The labelling degree ($Eu^{3+}$/IgG) was determined by measurement of the $Eu^{3+}$ concentration of conjugated antibody against a $Eu^{3+}$ calibrator with a DELFIA® system. A labelling degree of 11.5 was achieved. Labelled antibody has been found stable for several months when stored at +4° C. in Tris buffer, pH 7.4, containing bovine serum albumin as a stabilizer (0.1%).

EXAMPLE 3

Coating of Microtitration Plates With Anti-Hb Alpha-Chain Antibody

Microtitration strip wells (NUNC-IMMUNO™ STRIPS C 12 irradiated, type 4-77178) were coated with anti-Hb alpha-chain antibody (PerkinElmer Life and Analytical Sciences, Akron, USA), 1.0 µg antibody per well (in 0.2M $Na_2HPO_4$/0.2M $NaH_2PO_4$), at 37° C. in overnight incubation at pH 7. The coated strips were blocked by incubating with saturation buffer (50 mM $NaH_2PO_4$ containing 3% trehalose, 0.1% Germall II, and 0.1% bovine serum albumin) for overnight at room temperature (~22° C.), then aspirated and dried for at least overnight at 37° C. Air-tightly packed coated microtitration plates have been found stable for several months when stored at +4° C.

EXAMPLE 4

Immunoassay Concept

A schematic description of the immunoassay concept is shown in FIG. 1. The assay is an automated (AutoDELFIA®), HbS/A specific, dual-label immunoassay for detection of HbS and HbA variants from dried blood spot specimens (DBSS). The immunoassay was performed in the coated microtitration strip wells and specific Hb variants were detected using differently labelled anti-Hb variant antibodies. In the first incubation, all Hb from sample (one 3.2 mm DBSS) was captured onto solid support via anti-Hb α-chain coated to the microtitration wells (example 3) by eluting the DBSS with 200 µL water for 30 minutes (slow shaking). After disk remove and 2 washing cycles, HbS and HbA variants were detected using Eu and Sm labelled anti-HbS and anti-HbA antibodies, respectively (examples 1 and 2) by incubating 100 ng/well/labelled antibody, $V_{tot}$=100 µL for 45 minutes (slow shaking). After 6 washing cycles, Enhancement Solution was dispensed and the plate was incubated for another 15 minutes (slow shaking) prior to measurement of time-resolved fluorescence.

EXAMPLE 5

Specificity of the Anti-HbS Antibody

If the aim is to use immunoassay concept in the detection of HbS variant, the specificity of a given anti-HbS antibody is of ultimate importance. Thus, we tested some neonatal samples known to have different Hb variant using a HbS/A specific, dual-label immunoassay for detection of HbS and HbA variants from DBSS. The immunoassay was performed in the coated microtitration strip wells and specific Hb variants were detected using differently labelled anti-Hb variant antibodies. In the first step, all Hb from a given sample (one 3.2 mm DBSS/sample) was eluted in the non-coated microtitration plate wells with 200 µL water for 30 minutes (slow shaking). Then 10 µL sample eluate+90 µL Casein Buffer was dispensed to the anti-Hb α-chain coated microtitration wells (Example 3) and incubate for 30 minutes at room temperature (slow shaking). After 4 washing cycles, HbS and HbA variants were detected using Eu and Sm labelled anti-HbS and anti-HbA antibodies, respectively (Examples 1 and 2) by incubating 100 ng/well/labelled antibody, $V_{tot}$=100 µL for 45 minutes (slow shaking). After 4 washing cycles, Enhancement Solution was dispensed and the plate was incubated for another 5 minutes (slow shaking) prior to measurement of time-resolved fluorescence.

Table 1 shows the Eu- and Sm-signals obtained. Clearly, anti-HbS antibody used (Eu-labelled) recognises only carrier samples, i.e. FAS samples (signal range for FAS 8514-30202 vs. other variants mean 3107). However, all samples tested contained HbA, evidenced as positive Sm-signal. In conclusion, this experiment demonstrates the specificity of anti-HbS monoclonal antibody.

EXAMPLE 6

Specificity & Cross-Reactivity of the Hb Variant Specific Antibodies

If dual-label immunoassay system is to be used, one have to be sure that the used antibodies do recognise their target molecules with high specificity and that they do not interfere each other. The results shown here were obtained by using essentially the same assay concept as in example 5. Minor modifications were; after elution, 20 µL of sample eluate +80 µL Casein Buffer was dispensed to the coated microtitration plate. Also, labels were used in different concentrations and combinations (see Table 2). The sample is from normal, healthy subject, i.e. major hemoglobin present is HbA, with minor amounts of $HbA_2$.

As can be read from the Table 2, increasing concentrations of HbS specific Eu-labelled antibody do not interfere the measured Sm-signal that remains constant (range 8884-9418 cps). Similarly, Eu-background remains relatively constant (range 918-1873 cps) when two labelled antibodies are present. However, when only anti-HbS antibody is present, some cross-reactivity between HbA and anti-HbS antibody can be seen. In conclusion, this experiment demonstrate that both used antibodies, anti-HbS and anti-HbA antibodies, when used in combination, recognise their specific target molecule, i.e. HbS and HbA respectively, and that the presence of the either antibody does not interfere the binding of the other antibody.

EXAMPLE 7

Preparation & Testing of Calibrators

Figure 2A:
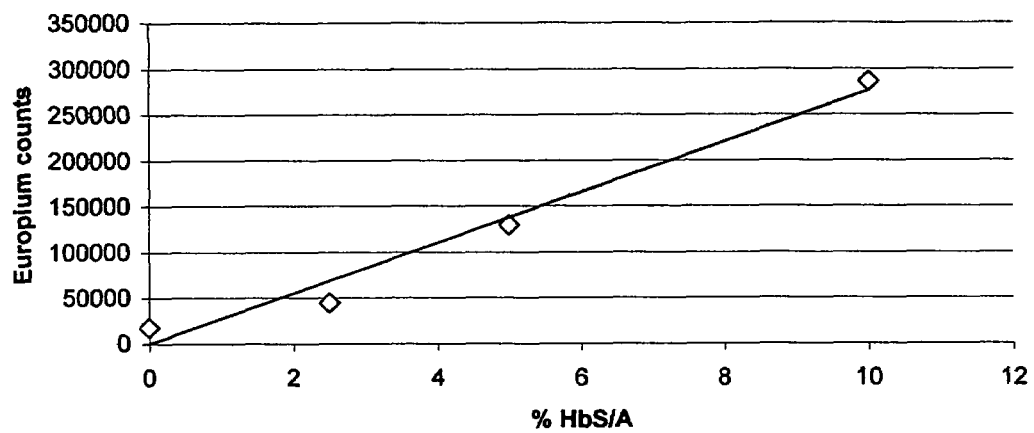
FIG. 2 shows two standard curves for two different labels (FIG. 2A Eu and FIG. 2B Sm), which are suitable for use in an assay according to the present invention.
Figure 2B:
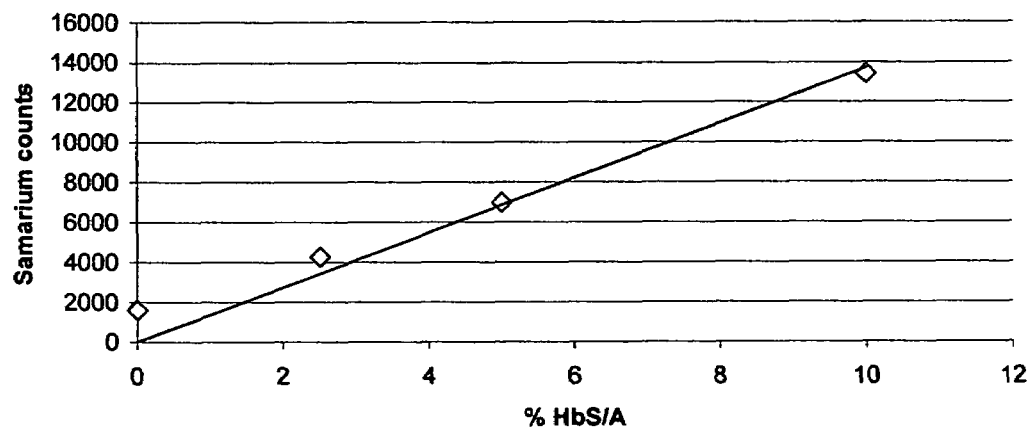

The ratio, say HbA to HbS ratio, can be calculated either using raw data (direct counts) obtained or by normalising the obtained counts to % hemoglobin using HbS and HbA specific calibrators. The first option, though simple, has some drawbacks such as different signal yields per molecule. The latter option gives better indicative measures (only semi-quantitative), but is rather difficult to carry out. In this example, we have developed HbS and HbA specific calibrators using pure HbA and HbS blood samples were prepared by diluting serially with chicken blood (the antibodies used are known to be non-reactive against chicken Hb) and finally spotting the blood to filter paper (S&S 903). These serial dilution included 0, 2.5, 5.0, and 10.0% of HbA or HbS. Furthermore, a similar series of calibrators having 0, 2.5, 5.0, and 10.0% of both HbA and HbS was prepared. The prepared calibrators were assessed as described in Example 4. The results of the individual HbA and HbS calibrators are shown in FIG. 2.

These results demonstrate that the used method can detect as low as 2.5% Hb proportions. Even though these prepared calibrators contain a specific total Hb concentration, unknown samples having different total Hb concentrations can be measured against these curves, but only if the ratio is calculated (ratio calculation eliminates the effect of varying total Hb concentrations). The percentage results obtained against these calibrators are therefore only indicative of a given Hb variant concentration.

EXAMPLE 8

Feasibility Test

To show the feasibility of the present invention, some known newborn samples (assessed using IEF) together with prepared calibrators having both HbA and HbS (Example 7) were analysed using the protocol described in example 4.

Table 3 shows both raw data (counts per second) as well as results normalised against prepared calibrators. Moreover, the HbA/HbS ratios have been calculated using both options. As can be seen, sickle cell carrier samples can easily be detected and differentiated from other samples using the method of present invention. When the ratio was calculated using raw data, the lowest non-afflicted ratio was 1.3, whereas ratios from FAS (sickle carrier) sample ranged from 0.06-0.25. Thus, according to this preliminary data, the first ratio (1.3) could be the cut-off level A and the ratio of 0.06 could be used as the cut-off level B. When the ratio was calculated using calibrators, the result was even more clearer: the lowest non-afflicted ratio was 27.9, whereas ratios from FAS (sickle carrier) sample ranged from 1.9-5.2. This could be interpreted as follows; 27.9 would be the cut-off level A, and 1.9 would be the cut-off level B. In both case, any sample having HbA/HbS ratio above cut-off level A is interpreted as normal (in term of sickle cell disease, SCD), the ratios between the two cut-off values are interpreted as sickle cell disease carriers and the ratios below cut-off level B are interpreted as sickle cell disease. The cut-off level B could be regarded as optional since in terms of sickle cell screening, the cut-off level A is of greatest importance by determining any sample that should be subjected to further analysis.

EXAMPLE 9

Clinical Feasibility Test

To show the clinical feasibility of the present invention, some known newborn samples (assessed using IEF) together with prepared calibrators having both HbA and HbS (Example 7) were analysed using the protocol described in example 4.

A total number of 498 neonatal samples were assessed. For each sample, the A to S ratio was calculated according to the individual (HbS and HbA) percentage results. Total through-put time for the 498 samples was 4h 18 minutes. Of the 498 samples, 366 were previously reported as normal (FA), 83 as SCD carriers (FAS) and 4 as SCD (FS or FSC). A number of other variants were also present in the study population (see Table 4). The results have been confirmed both using IEF and HPLC. Preliminary cut-off values were used in this feasibility study. Ratio cut-off level B (ratio<1.0) was utilized to identify SCD samples, whereas ratio cut-off level A (ratio between 1 and 4) was used to identify HbS carriers. If the ratio was greater than 4, these samples were reported as normal. Also, an additional parameter was used to identify abnormal samples, i.e. when HbA % was suspiciously low concomitant with no HbS % present, the sample is reported as repeat.

Table 4 shows the results of this clinical feasibility study. If the pre-sent assay is to be used as a primary screen for neonatal SCD, all the affected samples found. We identified all SCD carriers (one carrier sample was false identified as SCD) and SCD samples, whereas all the normal samples were identified either as normal (355/366) or repeat (11/366).

The overall repeat rate for the normal samples was 11/366~3%. Of the other Hb variants, 23/39 were noticed to be abnormal (repeat note), ~59%. Among these, ⅔ of FAC samples and ½ of Barts samples were detected, whereas the number of other variants was too low to draw any conclusions.

TABLE 1

| Sample | Eu-measurement | | | Sm-measurement | | |
|---|---|---|---|---|---|---|
| | counts | avg | cv % | counts | avg | cv % |
| FAS1 | 18187 | 15134 | 29 | 5256 | 4860 | 12 |
| | 12080 | | | 4465 | | |
| FAS2 | 23516 | 21779 | 11 | 4610 | 4154 | 16 |
| | 20042 | | | 3697 | | |
| FAS3 | 4521 | 8514 | 66 | 1135 | 1111 | 3.1 |
| | 12507 | | | 1086 | | |
| FAS4 | 13256 | 11374 | 23 | 3080 | 2807 | 14 |
| | 9491 | | | 2534 | | |
| FAS5 | 19508 | 21531 | 13 | 2020 | 1974 | 3.3 |
| | 23554 | | | 1928 | | |
| FAS6 | 31862 | 30202 | 7.8 | 2777 | 2934 | 7.6 |
| | 28542 | | | 3092 | | |
| FA Barts7 | 3427 | 3219 | 9.2 | 4884 | 4540 | 11 |
| | 3010 | | | 4195 | | |
| FAC13 | 2830 | 2985 | 7.3 | 4341 | 4232 | 3.6 |
| | 3139 | | | 4124 | | |
| FAE19 | 3447 | 3191 | 11 | 3314 | 3571 | 10 |
| | 2935 | | | 3829 | | |
| FAG25 | 3157 | 3631 | 18 | 8222 | 7927 | 5.3 |
| | 4104 | | | 7631 | | |
| FAD31 | 2564 | 2509 | 3.1 | 3222 | 2978 | 12 |
| | 2453 | | | 2734 | | |

TABLE 2

| Sample Ke549, dilution 1:5, (20 µl + 80 µl) | | | | | | | | |
|---|---|---|---|---|---|---|---|---|
| | | Sm-fluorescence | | | | | Eu-fluorescence | | |
| | | counts | avg | cv % | | | counts | avg | cv % |
| Sm-HbA 100 ng/w | Eu-HbS 10 ng/w | 9251 9584 | 9418 | 2.5 | Sm-HbA 100 ng/w | Eu-HbS 10 ng/w | 910 925 | 918 | 1.2 |
| | Eu-HbS 25 ng/w | 8808 9091 | 8950 | 2.2 | | Eu-HbS 25 ng/w | 2629 1014 | 1822 | 63 |
| | Eu-HbS 50 ng/w | 8554 9814 | 9184 | 10 | | Eu-HbS 50 ng/w | 1449 2117 | 1783 | 26 |
| | Eu-HbS | 9599 | 9208 | 6.0 | | Eu-HbS | 8236 | 4871 | 98 |

TABLE 2-continued

Sample Ke549, dilution 1:5, (20 µl + 80 µl)

| | Sm-fluorescence | | | | Eu-fluorescence | | |
|---|---|---|---|---|---|---|---|
| | counts | avg | cv % | | counts | avg | cv % |
| 75 ng/w | 8817 | | | 75 ng/w | 1505 | | |
| Eu-HbS | 8851 | 8884 | 0.5 | Eu-HbS | 2023 | 1873 | 11 |
| 100 ng/w | 8916 | | | 100 ng/w | 1723 | | |
| Eu-HbS | 338 | 334 | 1.7 | Eu-HbS | 5472 | 5654 | 4.6 |
| 100 ng/w | 330 | | | 100 ng/w | 5836 | | |

TABLE 3

| Sample | HbS cps | % HbS | HbA cps | % HbA | RATIO cps | RATIO % | Result |
|---|---|---|---|---|---|---|---|
| FAS | 296938 | 6.9 | 36984 | 21.6 | 0.12 | 3.1 | carrier |
| FAS | 251710 | 6.2 | 44240 | 32.4 | 0.18 | 5.2 | carrier |
| FAS | 114163 | 3.8 | 22136 | 9.4 | 0.19 | 2.5 | carrier |
| FAS | 141319 | 4.3 | 35976 | 20.4 | 0.25 | 4.7 | carrier |
| FAS | 275151 | 6.6 | 37372 | 22.1 | 0.14 | 3.3 | carrier |
| FAS | 627029 | 13.9 | 40155 | 25.8 | 0.06 | 1.9 | carrier |
| FABart's | 20387 | 0.5 | 41224 | 37.4 | 2.02 | 74.8 | non-afflicted |
| FABart's | 21265 | 0.5 | 48955 | 42.2 | 2.30 | 84.4 | non-afflicted |
| FABart's | 20545 | 0.5 | 51877 | 49.6 | 2.53 | 99.2 | non-afflicted |
| FABart's | 19056 | 0.4 | 47541 | 39 | 2.49 | 97.5 | non-afflicted |
| FABart's | 29107 | 0.9 | 43601 | 31.3 | 1.50 | 34.8 | non-afflicted |
| FABart's | 19693 | 0.4 | 46585 | 36.9 | 2.37 | 92.3 | non-afflicted |
| FAC | 18149 | 0.4 | 47359 | 38.6 | 2.61 | 96.5 | non-afflicted |
| FAC | 18172 | 0.4 | 33298 | 17.6 | 1.83 | 44.0 | non-afflicted |
| FAC | 18369 | 0.4 | 40146 | 25.8 | 2.19 | 64.5 | non-afflicted |
| FAC | 17203 | 0.3 | 36318 | 20.8 | 2.11 | 69.3 | non-afflicted |
| FAC | 19048 | 0.4 | 41836 | 28.3 | 2.20 | 70.8 | non-afflicted |
| FAC | 14411 | 0.2 | 22381 | 9.6 | 1.55 | 48.0 | non-afflicted |
| FAE | 19493 | 0.4 | 50064 | 44.9 | 2.57 | 112.3 | non-afflicted |
| FAE | 22608 | 0.6 | 46401 | 36.6 | 2.05 | 61.0 | non-afflicted |
| FAE | 18912 | 0.4 | 40487 | 26.3 | 2.14 | 65.8 | non-afflicted |
| FAE | 22529 | 0.6 | 45790 | 35.3 | 2.03 | 58.8 | non-afflicted |
| FAE | 27160 | 0.8 | 47136 | 38.1 | 1.74 | 47.6 | non-afflicted |
| FAE | 24201 | 0.6 | 45063 | 33.9 | 1.86 | 56.5 | non-afflicted |
| FAG | 21789 | 0.5 | 75371 | 184.1 | 3.46 | 368.2 | non-afflicted |
| FAG | 21214 | 0.5 | 47501 | 38.9 | 2.24 | 77.8 | non-afflicted |
| FAG | 29447 | 0.9 | 45046 | 33.9 | 1.53 | 37.7 | non-afflicted |
| FAG | 27793 | 0.8 | 37557 | 22.3 | 1.35 | 27.9 | non-afflicted |
| FAG | 19628 | 0.4 | 34834 | 19.2 | 1.77 | 48.0 | non-afflicted |
| FAG | 22391 | 0.6 | 42606 | 29.6 | 1.90 | 49.3 | non-afflicted |
| FAD | 25424 | 0.7 | 45358 | 34.5 | 1.78 | 49.3 | non-afflicted |
| FAD | 25743 | 0.7 | 48257 | 40.6 | 1.87 | 58.0 | non-afflicted |
| FAD | 30082 | 0.9 | 41359 | 27.6 | 1.37 | 30.7 | non-afflicted |
| FAD | 25016 | 0.7 | 39468 | 24.8 | 1.58 | 35.4 | non-afflicted |
| FAD | 24626 | 0.7 | 46402 | 36.6 | 1.88 | 52.3 | non-afflicted |
| FAD | 31410 | 1 | 45323 | 34.4 | 1.44 | 34.4 | non-afflicted |

TABLE 4

| | NOTE Reported | | | |
|---|---|---|---|---|
| Sample | NORMAL | REPEAT | CARRIER | SCD |
| FAC | 9 | 17 | | |
| FAS | | | 82 | 1 |
| Barts | 7 | 6 | 2 | |
| FA | 355 | 11 | | |
| FAC Barts | | | 1 | |
| FAD | 1 | | | |
| FC | | 1 | | |
| FS | | | | 2 |
| FSC | | | | 2 |
| G-Philly | | 1 | | |

The invention claimed is:

1. A method for neonatal screening of hemoglobinopathies, comprising the following steps:

i) obtaining a blood sample taken from a newborn;
ii) adding at least one pair of labelled hemoglobin specific reagents, wherein the first and second members of said pair are differently labelled and specifically recognize a different hemoglobin variant, and a third reagent, wherein the third reagent is a monoclonal antibody recognizing the hemoglobin α-chain;
iii) allowing the reagents to bind to hemoglobin present in the sample, thereby forming differentially labeled hemoglobin/reagent complexes;
iv) optionally, immobilizing the formed complexes;
v) detecting the signals generated by the labels in the formed differentially labelled hemoglobin/reagent complexes;
vi) calculating the ratio between the signals generated by the labels from each one of the differentially labelled hemoglobin/reagent complexes; and vii) determining whether the sample is derived from a non-afflicted subject or from an afflicted subject or carrier by correlating said ratio with at least one pre-selected cut-off value;

wherein said first member of said reagent pair is hemoglobin A (HbA) specific; said second member of said reagent pair is selected from the group consisting of hemoglobin S (HbS), hemoglobin C (HbC), hemoglobin D (HbD), hemoglobin E (HbE) and hemoglobin F (HbF) specific reagents; and said third reagent is coupled to a solid support or comprises a binding moiety for attachment to a solid support.

2. The method according to claim 1, wherein said sample is divided into two separate reaction chambers and a first member of said reagent pair and the third reagent are added to the first reagent chamber and a second member of said reagent pair and third reagent are added to the second reagent chamber.

3. The method according to claim 1, wherein the determination in step vii) is based on two cut-off values categorizing the test results into three groups: non-afflicted subjects, carriers and afflicted subjects.

4. The method according to claim 1, wherein said first member of said reagent pair, said second member of said reagent pair and said third reagent are selected from the group consisting of: monoclonal antibodies, aptamers and molecular imprints.

5. The method according to claim 4, wherein said first member of said reagent pair is a HbA specific monoclonal antibody, and said second member of said reagent pair is a HbS specific monoclonal antibody.

6. The method according to claim 1, wherein said first and second members of said reagent pair are labelled with a fluorescent, luminescent, chemiluminescent, radioactive, enzyme, colloidal sol or nanoparticle label.

7. The method according to claim 6, wherein said first and second members of said reagent pair are labelled with a label selected from the group consisting of: europium, samarium, terbium or dysprosium chelate.

8. The method according to claim 1, wherein said first and second members of said reagent pair are labelled with luminescent energy acceptor molecules and said third reagent is labelled with a luminescent energy donor molecule.

9. The method according to claim 8, wherein said luminescent energy acceptor molecule and said luminescent energy donor molecule form an acceptor/donor pair selected from the group consisting of: lanthanides/cyanine dyes, lanthnides/phycobiliproteins; and fluorescein/tetramethylrhodamine.

* * * * *